(12) United States Patent
Murer

(10) Patent No.: US 7,744,736 B2
(45) Date of Patent: Jun. 29, 2010

(54) METHOD OF MANUFACTURING A REFERENCE ELECTRODE

(75) Inventor: Sascha Murer, Steinhausen (CH)

(73) Assignee: Mettler-Toledo AG, Greifensee (CH)

( * ) Notice: Subject to any disclaimer, the term of this patent is extended or adjusted under 35 U.S.C. 154(b) by 1128 days.

(21) Appl. No.: 11/164,944

(22) Filed: Dec. 12, 2005

(65) Prior Publication Data

US 2007/0009689 A1    Jan. 11, 2007
US 2010/0068429 A9    Mar. 18, 2010

Related U.S. Application Data

(63) Continuation of application No. PCT/EP2004/051253, filed on Jun. 25, 2004.

(30) Foreign Application Priority Data

Jun. 25, 2004    (EP) ................ PCT/EP2004/051253

(51) Int. Cl.
*G01N 27/30*    (2006.01)
*C04B 41/87*    (2006.01)

(52) U.S. Cl. ...................... 204/435; 427/244

(58) Field of Classification Search .................. 204/435, 204/419; 427/58, 244–246
See application file for complete search history.

(56) References Cited

U.S. PATENT DOCUMENTS 4,170,537 A    10/1979    Simmons .................... 204/295

4,711,719 A    12/1987    Leenaars ................ 210/500.26

FOREIGN PATENT DOCUMENTS

| EP | 0 243 309 | 10/1987 |
| GB | 2 273 672 A | 6/1994 |
| JP | 59-107988 | 6/1984 |
| WO | WO 91/12879 | 9/1991 |

OTHER PUBLICATIONS

Okubo, et al. "Crack-free porous YSZ membrane via controlled synthesis of zirconia sol" J. Membr Sci 118 (Sep. 18, 1996) 151-157 (EPO Doc XP-002261486).
Anonymous, "Gels", Internet article (EPO Doc XP-00226187).

*Primary Examiner*—Kaj K Olsen
(74) *Attorney, Agent, or Firm*—Standley Law Group LLP

(57) ABSTRACT

A method of manufacturing a reference electrode which has a shaft into which a diaphragm body of a porous ceramic is incorporated is comprised of the following method steps: Impregnating the ceramic with a lyogel precursor prior to incorporating the ceramic body into the shaft, and subsequently transforming the lyogel precursor into a lyogel, from which the solvent is removed through a drying process. A reference electrode has a shaft that is filled with electrolyte, and a diaphragm body formed of a porous ceramic and containing a system of hollow spaces is incorporated into the wall of the shaft. The system of hollow spaces is filled at least partially with a material that is formed of a lyogel by drying and has at least one component that corresponds to the ceramic material.

27 Claims, No Drawings

METHOD OF MANUFACTURING A REFERENCE ELECTRODE

CROSS-REFERENCE TO RELATED APPLICATIONS

This application is a continuation of, and claims a right of priority under 35 USC § 120 and 35 USC §365 to, PCT/EP2004/051253, filed 25 Jun. 2004, which designates the United States, and which, in turn, claims a right of priority under 35 USC § 119 from European patent application 03 10 1864.1, filed 25 Jun. 2003.

TECHNICAL FIELD

The invention relates to a method of manufacturing a reference electrode having a shaft into which a diaphragm body of a porous ceramic is incorporated, and it also relates to a reference electrode having a shaft that is filled with electrolyte, wherein a diaphragm body formed of a porous ceramic and containing a system of hollow spaces is incorporated into the wall of the shaft.

STATE OF THE ART

Potentiometric measuring probes for the determination of analytes, for example hydrogen (pH value) or carbon dioxide, that are dissolved in liquids are often equipped with a reference electrode and a measuring electrode. The electrodes are configured in particular as glass electrodes which are equipped with a conductor element that is immersed in an electrolyte solution, wherein the electrical voltage potential that develops between the conductor element of the measuring electrode and the conductor element of the reference electrode serves as a measure for the ion concentration of the dissolved analyte. In this measurement, the electrolyte solution of the reference electrode is in contact with the medium that is to be measured (hereinafter referred to as the measurand medium), more specifically the measurand solution, wherein by means of an exchange of electrical charges, the reference element is also in electrical contact with the measurand medium. In connection with the exchange of electrical charges, a material exchange takes place. On the one hand the extent of the material exchange is kept as small as possible, and on the other hand one aims for the material exchange to occur preferably in the outward direction into the measurand solution. In particular, it is a known concept to create a connection by means of a diaphragm between a measurand solution and a reference electrolyte that is contained inside a reference electrode. A connection of this kind has on the one hand a good electrical conductivity and on the other hand also works as a barrier against an unwanted mixing of the measurand solution and the reference electrolyte (see for example: H. Galster, "pH-Messung" (*pH Measurement*), VCH Verlagsgesellschaft (Weinheim) 1990, pp. 83-84). A diaphragm of this type is often fused as a porous ceramic component into an opening in the wall of the reference electrode shaft that is primarily formed of glass.

Proven materials for use as diaphragms include above all porous ceramics of porcelain, aluminum oxide, spinel, forsterite, and in particular zirconia (used herein as a customary term for zirconium(IV) oxide, $ZrO_2$). Porous ceramics of so-called "stabilized zirconia", containing calcium oxide ("calcia") or magnesium oxide ("magnesia") and preferably yttrium oxide ("yttria") as a stabilizing additive, have been proven to be particularly advantageous.

Stabilized zirconia is distinguished by a good level of chemical corrosion resistance, in particular against alkaline media. Stabilized zirconia is furthermore temperature-resistant and has a coefficient of thermal expansion similar to that of soft glasses. Consequently, diaphragms of stabilized zirconia can be fused into glass housings of reference electrodes and the like without any problems.

Porous zirconia ceramics are manufactured by extruding wet oxide pastes, followed by the steps of drying and firing, or alternatively by a process of compacting oxide powders under isostatic pressure, followed by firing. The desired porosity is obtained through the selection of the particle size and by using a firing temperature where the pores that are present in the green part will not close themselves off completely but a sufficient degree of sintering will take place, so that the end product has an adequate mechanical integrity.

There is a need for diaphragms which in comparison to the previously known diaphragms have an even higher flow-through resistance without a significant decrease in the electrical conductivity. To meet this purpose, one would need porous ceramics which in comparison to the heretofore known ceramics have significantly smaller pores in conjunction with an adequate pore volume. However, attempts to manufacture this type of ceramics through a control over the ceramic raw material and/or the firing temperature have so far been unsuccessful.

Reducing the size of the ceramic pores, for example by using a longer sintering process, has the unavoidable consequence of a corresponding reduction of the electrical conductivity, because as the duration of this process is increased, the mean diameter as well as the frequency of the pores decrease strongly, leading to the result of a reduced conductivity cross-section.

According to a further known possibility, which the applicant has been using for an extended period of time, the pores of a diaphragm of a porous ceramic are reduced in size by means of polymers. Under this concept, the diaphragm is first fused into the glass shaft of the reference electrode, because if the fusing were performed at a later stage, it would destroy the polymer. However, as a disadvantage of this method, it has been observed that the conductivity decreases as the quantity of polymer absorbed in the diaphragm is increased.

As another known state-of-the-art measure for keeping the rate of material flow small though a reference electrode diaphragm, an electrolyte solution is used which has a higher degree of viscosity. The increase in viscosity is achieved by adding a thickening agent to the electrolyte, such as for example hydroxy ethyl cellulose (Natrosol®), or a water-soluble polymer such as for example polyacrylamide, agar, pyrolidone, or polyvinyl alcohol. The disadvantage of this type of a solution lies in the strong temperature dependence of the viscosity of the electrolyte which increases the ability of the electrolyte to flow out of the probe in cases where the latter is used in high-temperature applications. There is the further danger that the diaphragm will progressively become clogged up by the macromolecules that are dissolved in the electrolyte, where the so-called cluster diameter of a macromolecule as a rule exceeds the diameter of the pores of the diaphragm.

PRESENTATION OF THE INVENTION

The invention has the objective to propose an improved method for the manufacture of a reference electrode. The invention has the further objective to propose an improved reference electrode. Achieving the desired improvement entails avoiding the aforementioned drawbacks which occur on the one hand when the diaphragm is modified in accordance with the state of the art and on the other hand when an electrolyte of increased viscosity is used.

The foregoing objectives are accomplished with the method and by the reference electrode defined in the appended claims.

The method according to the invention is based on a controlled reduction of the pore size of a porous ceramic material from which a diaphragm body for a reference electrode is manufactured, wherein the reference electrode has a shaft, in particular a glass shaft or a polymer shaft, into which the diaphragm body is incorporated. The method includes the following steps:
a) Providing a porous ceramic body;
b) Impregnating the porous ceramic body with a lyogel precursor;
c) Transforming the lyogel precursor into a lyogel;
d) Removing the solvent by drying, and
e) after the diaphragm body has been completed in this manner, incorporating it in the shaft.

A conventional porous ceramic, which can be of a commercially available type if desired, serves as base material. This ceramic has an initial porosity which is determined by the existing pore structure, i.e., a system of hollow spaces extending throughout the ceramic body. The porous ceramic as provided at the start is subsequently impregnated with a lyogel precursor which in a next process step is transformed into a lyogel. The term "lyogel" in the present context should be understood as a generic term for a plurality of different gels which have different names depending on the type of their liquid component. The generic designation "lyogel" includes in particular the water-containing "aquagels" or "hydrogels" (see for example: J. Falbe, M. Regitz, editors, "Römpp Chemie Lexikon", Georg Thieme Verlag (Stuttgart) 1990, volume 2, p. 1511). Substances that would qualify as lyogel precursors include not only actual solutions, but also so-called "lyosols", with the precursors of water-containing aquagels being referred to as "aquasols", analogous to the terminology discussed above.

By filling the hollow spaces of the porous ceramic at least partially with lyogel, one obtains a porous ceramic with reduced pores.

With the method of a controlled reduction of the pore size, it becomes possible to use for the reference electrode an electrolyte without macromolecular thickening agents. The aforementioned problems of the strongly temperature-dependent viscosity and the clogging-up of the diaphragm are thereby circumvented.

Surprisingly, it has been found that the electric conductivity through the diaphragm of the reference electrode that is made in accordance with the foregoing method is nearly unchanged in comparison to the conductivity of a diaphragm in which the pore size has been reduced under a state-of-the-art method.

The reference electrode according to the invention is comprised of a shaft that is filled with electrolyte, in particular a glass- or polymer shaft in whose wall a diaphragm body made of a porous ceramic and containing a system of hollow spaces is incorporated, wherein the system of hollow spaces is filled at least partially with a material that is formed of a lyogel by drying and which has at least one component that corresponds to the ceramic material.

In particular, it is possible to select a degree of filling the ceramic with the lyogel which correlates to a desired pore size.

Allowing for the fact that, as a general rule, the system of hollow spaces in a porous ceramic has a multitude of channels and cavities of different sizes, the term "pore size" in the present context has to be understood as a measure for a distribution which can be characterized, e.g., by a mean value, a standard deviation or other statistic indicator values. Accordingly, the term "pore size reduction" likewise needs to be interpreted with the background of its distributive nature in mind.

Advantageous embodiments of the invention are defined in the dependent claims.

Dependent claims relate to preferred embodiments of the method according to the invention, as well as to preferred embodiments of the reference electrode according to the invention.

Under a preferred aspect of the invention, the method includes the further step of transforming the lyogel that has been formed out of the lyogel precursor into an aerogel, which is accomplished by removing solvent from the lyogel. An aerogel, in the sense of a dried gel with hardly any shrinkage in comparison to the lyogel, is present in the pores of the ceramic, because the spatial structure of the solid component that is initially present in the lyogel is substantially preserved in this transformation wherein the solvent is replaced by air or possibly by another gas (see likewise: J. Falbe, M. Regitz, editors, "Römpp Chemie Lexikon", Georg Thieme Verlag (Stuttgart) 1990, volume 2, p. 1511). Due to the fact that the micro-pores of the ceramic are filled at least partially with a nano-porous aerogel, a ceramic with a very fine porosity is obtained. If necessary, the sequence of steps consisting of impregnating the porous ceramic with a lyogel precursor, transforming the lyogel precursor into a lyogel, and transforming the lyogel into an aerogel is performed several times, achieving with each pass a further reduction in pore size until a pore size reduction has been obtained that conforms to a defined target value for a specific application.

The step of forming an aerogel is performed preferably by means of a drying phase in which the porous ceramic is subjected to a heat treatment. This is indicated in particular in all cases in which the diaphragm is fused in a later step into an electrode shaft of glass or the like.

The method can be performed in principle with different kinds of porous ceramics. Examples to be named here include: alumina/zirconia spinels, furthermore alumina, magnesia or silica either alone or in combinations such as for example silmanite ($Al_2O_3.SiO_2$), mullite ($3Al_2O_3.2SiO_2$), forsterite ($2MgO.SiO_2$), spinel ($MgO.Al_2O_3$), or cordierite ($2MgO.2Al_2O_3.5SiO_2$).

In the preferred way of practicing the inventive method, zirconia-based ceramics are used, in particular of stabilized zirconia, which contains calcium oxide (calcia) or magnesium oxide (magnesia), preferably yttrium oxide (yttria), as a stabilizing additive, which is of advantage primarily for certain electrochemical applications.

There are different kinds of lyogel precursors that can be used. For example, a lyosol can be used as lyogel precursor, in particular in the form of a stabilized aqueous suspension of nano particles that are selected from the group constituted by zirconia, zirconia/calcia, and zirconia/yttria. Alternatively, the lyogel precursor can also be introduced in the form of a solution. Used with preference as a lyogel precursor is an aqueous solution of zirconium, or an organic zirconyl compound, or a zirconium compound in an organic solvent.

The transformation of the lyogel precursor into the lyogel is preferably induced by destabilizing the lyosol, for example by changing the pH value. In the practical execution, it is particularly advantageous to effect the aforementioned change of the pH value by means of a base. As a base one could use an ammonia solution; as an alternative, however, one could also use a base from the group of the volatile organic amines, in particular isopropylamine, propylamine, tetramethyl amino methane, or triethylamine. Under a special embodiment of the invention, the base can be a gas.

If necessary, a gelating agent can be added to the lyogel precursor prior to impregnating the porous ceramic, whereby the desired transformation of the lyogel precursor into the lyogel is induced after the step of impregnating the ceramic.

The reference electrode according to the invention preferably has a diaphragm body of a porous ceramic that is based on zirconia, in particular stabilized zirconia.

In an advantageous embodiment of the reference electrode, the lyogel for reducing the pore size of the diaphragm body was selected from the group constituted of zirconia, zirconia/calcia, zirconia/magnesia, and zirconia/yttria.

Ways of Putting the Invention into Practice

The invention will hereinafter be described in more detail through practical examples.

EXAMPLE 1

Diaphragm rods of porous stabilized zirconia with a diameter of 1.1 mm and a length of 100 mm were put into a crystallizing bowl. The crystallizing bowl was then filled with zirconia sol, so that all of the diaphragm rods were completely submerged. The crystallizing bowl was subsequently placed into a vacuum exsiccator and for a period of 30 minutes, the air was driven out of the diaphragm rods. As a next step, the air was let into the exsiccator again, and the crystallizing bowl with contents was left there for another 30 minutes. After this waiting period, the rods where taken out of the crystallizing bowl with a pair of tweezers.

A beaker with a rounded opening was made ready and was filled with 100 ml of a concentrated aqueous base. Subsequently, the diaphragm rods were set into the glass beaker, then the glass beaker was covered with a watch glass and left standing overnight.

The next morning, the diaphragm rods were taken out of the glass beaker, laid on a watch glass and put into an oven that had been preheated to 80° C., and dried in the oven for 30 minutes. Finally, the diaphragm rods were laid into a muffle furnace that had been preheated to 500° C. and were left there for 45 minutes. After taking it out of the muffle furnace, the watch glass with the diaphragm rods was left to cool for 3 hours. This concludes a process of blocking or reducing the pores in the rods.

Subsequently, the ceramic rods were cut to a suitable size for the diaphragm body. It is considered self-evident that the process of the foregoing description is applicable not only to diaphragm rods but also to ceramic bodies that already have the appropriate size for a diaphragm body. The diaphragm body was fused into the shaft of the reference electrode. Alternatively, it can also be bonded in place with an adhesive.

EXAMPLE 2

The steps described in Example 1 were repeated, i.e., they were carried out with diaphragm rods that had already been subjected to one or more pore-reducing processes, until a prescribed degree of pore-size reduction was attained. For example, starting with diaphragm rods with a pore volume percentage of about 30% to 40% and a density of the solid skeleton structure of about 5.8 g/cm$^3$, diaphragm rods were produced whose pore volume percentage was reduced by one-half so that it amounted to 15% to 20%, with hardly any reduction at all in the density of the solid skeleton structure.

EXAMPLE 3

The process of keeping the diaphragm rods overnight in a glass beaker filled with 100 ml of a concentrated aqueous base, as described in Example 1, was realized in an alternative way where the diaphragm rods were not immersed in the base but were held above the surface of the liquid in the gaseous phase of the base, which allowed the gas to uniformly penetrate into the ceramic pores.

EXAMPLE 4

The following table presents a comparison between a diaphragm that has been treated in accordance with the foregoing examples and a non-treated diaphragm.

TABLE

Comparison between a non-treated and a treated diaphragm

|  | Non-treated diaphragm | Treated diaphragm |
| --- | --- | --- |
| Water flow-through rate (g/24 h) at a pressure difference of 5 bar | 1.5-2.0 | 0.2-0.4 |
| Electrical resistance (kOhm) | 5-10 | 5-10 |
| Open porosity (%) | 20-38 | 15-20 |

The foregoing results demonstrate that the treated diaphragm has a significantly smaller flow-through rate for water than the non-treated diaphragm, but that no difference can be found in regard to the electrical resistance. In other words, the treated diaphragm is distinguished by having a higher flow resistance without compromising the electrical conductivity.

What is claimed is:

1. A method of manufacturing a reference electrode, the reference electrode having a shaft into which a diaphragm body of a porous ceramic is incorporated, the method comprising the steps of:
   providing a porous ceramic body;
   impregnating the ceramic body with a lyogel precursor;
   transforming the lyogel precursor into a lyogel;
   removing solvent from the impregnation step by drying, to form the diaphragm body; and
   incorporating the diaphragm body into the shaft.

2. The method of claim 1, wherein the drying process transforms the lyogel into an aerogel.

3. The method of claim 2, wherein the porous ceramic comprises zirconia.

4. The method of claim 3, wherein the porous ceramic further comprises at least one of calcium oxide, magnesium oxide and yttrium oxide as a stabilizing additive.

5. The method of claim 4, wherein the lyogel precursor is an aqueous suspension of nano particles selected from the group consisting of zirconia, zirconia/calcia, zirconia/magnesia, and zirconia/yttria.

6. The method of claim 4, wherein the lyogel precursor is selected from a group consisting of an aqueous zirconium solution, an organic zirconyl compound and a zirconium compound in an organic solvent.

7. The method of claim 4, wherein the step of transforming the lyogel precursor into the lyogel occurs by a change of the pH value.

8. The method of claim 7, wherein a base is used to change the pH value.

9. The method of claim 8, wherein the base is an ammonia solution.

10. The method of claim 8, wherein the base is a volatile organic amine.

11. The method of claim 8, wherein the base is used in a gaseous state.

12. The method of claim 8, wherein the base is selected from the group consisting of isopropylamine, propylamine, tetramethyl amino methane, and triethylamine.

13. The method of claim 1, wherein the lyogel precursor used to impregnate the porous ceramic includes a gelating agent.

14. The method of claim 1, wherein the porous ceramic comprises zirconia.

15. The method of claim 14, wherein the porous ceramic further comprises at least one of calcium oxide, magnesium oxide and yttrium oxide as a stabilizing additive.

16. The method of claim 1, wherein the lyogel precursor is an aqueous suspension of nano particles selected from the group consisting of zirconia, zirconia/calcia, zirconia/magnesia, and zirconia/yttria.

17. The method of claim 1, wherein the lyogel precursor is selected from a group consisting of an aqueous zirconium solution, an organic zirconyl compound and a zirconium compound in an organic solvent.

18. The method of claim 1, wherein the step of transforming the lyogel precursor into the lyogel occurs by a change of the pH value.

19. The method of claim 18, wherein a base is used to change the pH value.

20. The method of claim 19, wherein the base is an ammonia solution.

21. The method of claim 19, wherein the base is a volatile organic amine.

22. The method of claim 19, wherein the base is selected from the group consisting of isopropylamine, propylamine, tetramethyl amino methane, and triethylamine.

23. The method of claim 19, wherein the base is used in a gaseous state.

24. A reference electrode comprising: a shaft adapted to be filled with electrolyte, a wall of the shaft having a diaphragm body incorporated therein, the diaphragm body being formed of a porous ceramic and providing a system of hollow spaces wherein the system of hollow spaces is filled at least partially with a material formed of a lyogel by drying, the material comprising at least one component that corresponds to the ceramic material.

25. The reference electrode according to claim 24, wherein the ceramic is formed of zirconia.

26. The reference electrode of claim 25, wherein the lyogel is selected from at least one of zirconia, zirconia/calcia, zirconia/magnesia, and zirconia/yttria.

27. The reference electrode of claim 24, wherein the lyogel is selected from at least one of zirconia, zirconia/calcia, zirconia/magnesia, and zirconia/yttria.

* * * * *